United States Patent [19]
Arakaki et al.

[11] Patent Number: 6,103,489
[45] Date of Patent: Aug. 15, 2000

[54] CELL-FREE PROTEIN SYNTHESIS SYSTEM WITH PROTEIN TRANSLOCATION AND PROCESSING

[75] Inventors: Richard Arakaki, Honolulu, Hi.; Xiangjun Zhou, Sunnyvale, Calif.

[73] Assignee: University of Hawaii, Hi.

[21] Appl. No.: 09/045,083

[22] Filed: Mar. 20, 1998

Related U.S. Application Data

[60] Provisional application No. 60/041,353, Mar. 21, 1997.
[51] Int. Cl.[7] ............................... C12P 21/00; C12N 5/06
[52] U.S. Cl. .......................................... 435/68.1; 435/325
[58] Field of Search ..................................... 435/68.1, 325

[56] References Cited

PUBLICATIONS

Frydman et al., "Folding of nascent polypeptide chains in a high molecular mass assembly with molecular chaperones," *Nature* 370:111–117 (1994).

Frydman and Hartl, "Principles of chaperone–assisted protein folding: differences between in vitro and in vivo mechanisms," *Science* 272:1497–1502 (1996).

Goldstein and Kahn, "Initial processing of the insulin receptor precursor in vivo and in vitro," *J. Biol. Chem.,* 263:12809–12812 (1988).

Laemmli, "Cleavage of structural proteins during the assembly of the head of bacteriophage T4," *Nature* 227:680–685 (1970).

Matthews and Colman, "A highly efficient, cell–free translation/translocation system prepared from Xenopus eggs," *Nucl. Acids Res.,* 19:6405–6412 (1991).

Murray and Kirschner, "Cyclin synthesis drives the early embryonic cell cycle," *Nature* 339:275–280 (1989).

Zhou et al., "In vitro translation of the human insulin proreceptor results in N–linked glycosylation without dimer formation," *Biochem. Biophys. Res. Comm.,* 192:1453–1459 (1993).

Tsuda et al., "The in vitro synthesized and processed human insulin receptor precursor binds insulin," *FEBS Lett.,* 457:13–17 (1999).

Zhou et al. (Dec. 1996) Mol. Biol. of the Cell, vol. 7, p. 439a, abstract 2552.

*Primary Examiner*—Elizabeth Slobodyansky
*Attorney, Agent, or Firm*—Medlen & Carroll, LLP

[57] ABSTRACT

An amphibian egg extract is added to a cell-free translation system to obtain in vitro translocation and processing of newly synthesized peptide. The egg extract produces near complete signal sequence and N-linked carbohydrate processing of protein. Egg extract microsomes provide for protein translocation.

3 Claims, 4 Drawing Sheets

CELL-FREE PROTEIN SYNTHESIS SYSTEM WITH PROTEIN TRANSLOCATION AND PROCESSING

This application for patent under 35 U.S.C. 111(a) claims priority to Provisional Application Ser. No. 60/041,353, filed Mar. 21, 1997 under 35 U.S.C. 111(b).

FIELD OF INVENTION

The present invention relates to a system and methods for analysis of newly synthesized polypeptides and for production of mature proteins.

BACKGROUND OF THE INVENTION

The wide-ranging effort to sequence the human genome has generated new sub-fields of research and new research challenges. The sequencing effort identifies new genes which encode heretofore unknown proteins. Efforts at characterizing the proteins focus on the important issue of determining what the protein does in the body and in what tissues, cells, or subcellular organelles the protein is found. Thus, with the human genome project proceeding at full steam, there is increased need for research methods to characterize new proteins.

The protein-encoding genes, which are made of two strands of material called deoxyribonucleic acid (DNA), encode information used to construct proteins via an intermediate which is a molecule of ribonucleic acid (RNA). The process of transcribing the information encoded in one strand of the DNA of a gene into a complementary molecule, the RNA, is called "transcription" and the resulting RNA strand is referred to as a "transcript" or as "messenger RNA" (mRNA). "Translation" refers to the process by which the information encoded in the mRNA transcript is used, as a blueprint, to synthesize a polypeptide chain. One or more polypeptide chains compose a protein.

Following synthesis of the polypeptide chain, the chain folds into its unique conformation that is characteristic for each protein and may undergo further modifications by processes known as "post-translational processing." If these modifications occur as the polypeptide is being synthesized, then the term "co-translational processing" is used. Another aspect to the maturation of a polypeptide chain into a mature protein is "translocation," the movement of the polypeptide chain across a biological membrane. Some aspects of translational processing occur contemporaneously with translocation and, in talking about these processing events, the term "co-translational translocation" is used.

To study the general phenomenon of protein synthesis and processing in the laboratory, cell-free systems are used. There are a number of known cell-free systems for translation, which are prepared from a variety of sources, including *E. coli,* wheat germ, Xenopus eggs, rabbit reticulocyte, and HepG2 cells (Frydman, J. and Hartl, F U, (1996) *Science* 272:1497–1502; Goldstein, B. J. and Kahn, C. R. (1988) *J. Biol. Chem.* 263:12809–12). Two widely used in vitro translation systems are rabbit reticulocyte lysate (RRL) and wheat germ extract. The RRL and wheat germ extract systems are commercially available as translation kits and are relatively straightforward to use. These kits allow for translation of a nascent polypeptide.

In cells, the biosynthesis of many proteins requires co-translational translocation across membranes of an organelle called the endoplasmic reticulum (ER) for proper processing. In cell-free systems, in place of the ER, microsomal membranes are used, which are equivalent to the ER in that they contain a high percentage of ER membrane which have been isolated by centrifugation.

Cell-free translation systems such as RRL contain very few ER membrane equivalent, so that in order to observe co-translational translocation and core glycosylation processing, an exogenous source of microsomes is needed (Zhou, X., Baker, N. K., and Arakaki, R. F. (1993) *Biochem. Biophys. Res. Comm.* 192:1453–1459). Examination of co- and post-translational protein modifications of polypeptides has been performed by the addition of heterogeneous canine pancreatic microsome membranes (MM). Canine pancreatic microsomal membranes have been used in combination with RRL to study the post-translational processing of both secretory proteins and membrane proteins, but the processing efficiency for membrane proteins is limited. Since a large proportion of proteins are either secretory or membrane-bound proteins, and since biosynthesis of these proteins requires serial posttranslational modifications initiated in the ER, the use of efficient cell-free translation and translocation methods is needed.

The RRL system was used to study the structure and functional characteristics of the human insulin receptor protein (hINSR) during its biosynthesis (Zhou, X., Baker, N. K., and Arakaki, R. F. (1993) *Biochem. Biophys. Res. Comm.* 192:1453–1459). Processing of the hINSR precursor protein by the addition of microsomal membranes was of consistently low efficiency. This may reflect the fact that the hINSR precursor is a large transmembrane protein (i.e., it spans the entire width of a biological membrane in which it is embedded) of about 160 kDa, and processing by microsomal membranes requires multiple and extensive N-linked glycosylation steps to yield the 190 kDa pro-receptor. Large transmembrane proteins, such as hINSR, may exceed the capacity of canine microsomal membranes to efficiently process the protein synthesized in a RRL system.

A further problem with canine microsomal membranes, is that the low efficiency of protein processings requires that additional steps be performed, such as lectin chromatography to separate and isolate the 190 kDa pro-receptor from the 160 kDa nascent protein receptor precursor.

SUMMARY OF THE INVENTION

The present invention relates to a system and methods for analysis of newly synthesized polypeptides and for production of mature proteins. In a heterologous system contemplated as the invention, polypeptide synthesis is performed in a cell-free translation system from a first organism and polypeptide translocation and processing are performed by use of a translocation and processing system derived from a second organism. Preferably, the cell-free translation system is reticulocyte lysate or a wheat germ extract. Wheat germ extract is useful for translation of small mRNA transcripts. The polypeptide translocation and processing system is an amphibian egg extract, preferably from a frog, and most preferably from *Xenopus laevis*. A heterologous system, according to the invention, also comprises a nucleic acid sequence which is capable of being translated by the cell-free translation system. Preferably the translatable nucleic acid sequence is mRNA. Alternatively, the nucleic acid sequence is cDNA and a messenger RNA polymerase is included as a component of the heterologous system.

As used herein, the term "mRNA transcript" refers to eukaryotic RNA that is produced by the process of transcription of a protein-coding DNA template by the enzyme RNA polymerase II and that has undergone post-transcriptional processing including splicing to remove intron sequences and addition of a 5'-cap structure and a 3'-poly(A) tail. As used herein, the term "large mRNA transcript" refers to transcripts giving rise to a protein larger than about 60 kDa, while the term "small mRNA transcript" refers to transcripts giving rise to a protein smaller than about 60 kDa.

The invention is also contemplated as a process for in vitro synthesis, translocation and processing of a protein, comprising, introducing a translatable nucleic acid sequence into a cell-free translation system to obtain a translation product; and introducing an amphibian egg extract into the cell-free translation system containing the translation product, whereby the translation product is translocated and processed to a protein.

In another embodiment, the invention is contemplated as a process for characterizing the function of a protein-coding gene product from its molecular composition, comprising: introducing the gene into a cell-free translation system to obtain a transcription translation product; introducing an amphibian egg extract containing membranes derived from endoplasmic reticulum into the cell-free translation system containing the translation product, whereby the translation product is translocated and processed to a protein; detecting the location of the protein as membrane-bound or unbound; and correlating the location of the protein to an aspect of its function. According to the method of the invention, the location of a protein which is entirely enveloped by the membranes is correlated with a secretory function. According to the method of the invention, the location of a protein which is embedded in the membranes is correlated with a membrane protein.

DETAILED DESCRIPTION OF THE INVENTION

Figure 1:
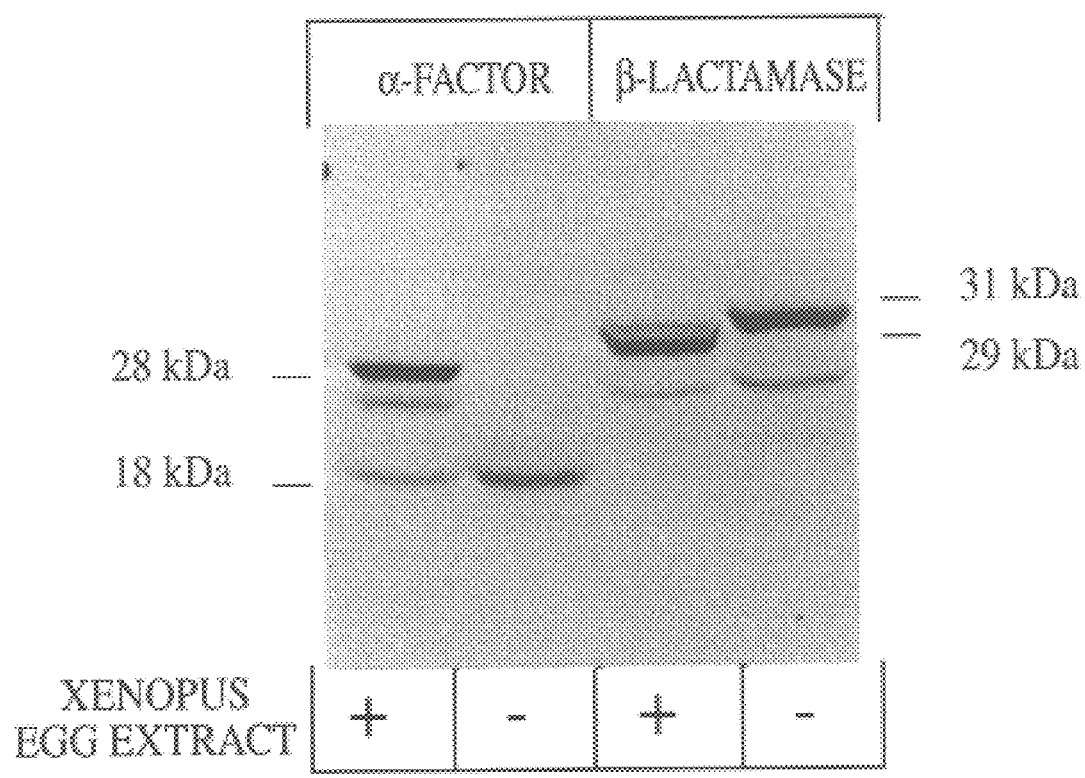
FIG. 1 is a gel from SDS-PAGE, representing signal sequence and N-linked glycosylation processing of β-lactamase and α-factor by Xenopus egg extract.

The present invention relates to a system and methods for analysis of newly synthesized polypeptides and for production of mature proteins. A heterologous system is provided, comprised of an efficient cell-free translation system along with amphibian egg extract which allows for in vitro synthesis of a polypeptide and for processing and translocation of the polypeptide to provide a protein of interest.

It is not intended that the cell-free translation system be limited in any fashion other than that its source is different from that of the egg extract. Examples of appropriate sources of the cell-free translation system include *E. coli,* wheat germ, Xenopus eggs, rabbit reticulocyte, and HepG2 cells. The appropriate source for the cell-free translation system is one that has high productivity in translating the mRNA transcript of interest. Consideration should be given to the size of the mRNA transcript and the efficiency of the cell-free translation system in translating that size transcript (e.g., the wheat germ system is more efficient at synthesis of lower molecular weight proteins). In some cases, choice of the appropriate cell-free system may be made by a comparison of the translation efficiency of several cell-free translation systems with the mRNA transcript of interest. Cell-free translation kits are commercially available (e.g., Promega Corp.).

It is also not intended that the amphibian egg extract be limited to a particular source. However, the appropriate source will have ER equivalent microsomal membranes and preferably, components which act in conjunction with the membranes to perform protein processing and translocation. Protein processing, as used herein, refers to modifying the translation product in a manner to produce a mature protein. Representative protein processing reactions include signal peptide cleavage, glycosylation, insertion into membranes, and protein folding and assembly. As used herein, "mature protein" refers to a functional protein which results from modification of the primary, secondary and/or tertiary structure of a polypeptide translated from an mRNA transcript. It is contemplated that if polypeptide processing components are added to the heterologous system, the egg extract is capable of using the factors in processing and translocation reactions. The components contemplated include, but are not limited to enzymes, factors and co-factors, intermediates (e.g., oligosaccharide intermediates), recognition proteins.

Besides the capability for processing and translocation, preferred egg extract should demonstrate stability and consistent performance. A preferred source for the egg extract is *Xenopus laevis*. The Xenopus egg extract is stable to freezing at −70° C. and to repeated freezing and thawing. Furthermore, Xenopus egg extract provides better performance than the conventional canine pancreas microsomal in vitro system for translocating and processing polypeptides.

As an alternative source of microsomes to canine pancreas microsomal membranes, Xenopus egg extract is not only advantageous in its productivity but also in the fact that there is no required animal sacrifice. An average of 20–40 ml of loosened eggs can be collected from frog ovulation induced by hormone injection, which can be repeated once a month. Moreover, the fractionation of Xenopus egg extract is done on a common bench-top centrifuge which is available virtually in every molecular biology laboratory. The simplicity and low-technology of this method, plus its high quality in processing efficiency and consistency, make it an excellent component for the heterologous system of the invention.

For identifying an unknown protein, use of Xenopus egg extract in a heterologous cell free system has advantages over the technique of microinjection of mRNA transcripts into Xenopus oocytes. The heterologous cell free system is much simpler, not requiring the technical instrumentation and expertise of microinjection and it provides much greater productivity where the object is to process large amounts of nascent polypeptide. Furthermore, where the object is to study the characteristics of an unknown polypeptide, the heterologous system allows for a pause between translation and processing/translocation reactions to allow for characterization of the nascent polypeptide, whereas microinjection into Xenopus oocytes does not. The ability to pause for characterization of the nascent polypeptide also distinguishes the heterologous system over cell-free systems that utilize egg extract to translate, process and translocate in a single operation (Matthews, G. M. and Colman, A. (1991) *Nucleic Acids Res.* 19:6405–6412).

Experimental

The following examples serve to illustrate certain preferred embodiments and aspects of the present invention and are not to be construed as limiting the scope thereof.

The pSP64-hINSR plasmid was a gift of Dr. Graeme Bell (Howard Hughes Medical Institute, University of Chicago). Rabbit reticulocyte lysate, SP6 RNA polymerase, RNase inhibitor, and canine pancreatic microsomal membranes, N-linked glycosylation control mRNA of α-mating factor from *S. cerevisiae* and signal peptide cleavage control mRNA of β-lactamase from *E. coli* were purchased from Promega Corporation (Madison, Wis.). Pregnant mare's serum gonadotropin (PMSG), human chorionic gonadotropin (hCG), phenylmethylsulfonyl fluoride (PMSF), and Aprotinin were supplied by Sigma (St. Louis, Mo.). The translation grade [$^{35}$S]-methionine was purchased from Dupont NEN (Boston, Mass.). Trypsin (TPCK treated, 204 U/mg) was supplied by Worthington Biochemical Corp. (Freehold, N.J.). Materials for polyacrylamide gel electrophoresis (PAGE) were obtained from Bio-Rad (Richmond, Calif.). All other chemicals were reagent grade.

Example 1

Comparison of *Xenopus Laevis* Egg Extract and Canine Microsomal Membranes for In Vitro Translocation and Processing Pretreatment of Adult Female Frogs and Preparation of *Xenopus Laevis* Egg Extract This study was approved by the Laboratory of Animal Services of the University of Hawaii. Adult female *Xenopus laevis* were obtained from Nasco (Fort Atkinson, Wis.). The Xenopus eggs were obtained from frogs by injection of 100 U of pregnant mare's serum gonadotropin (PMSG) for oocyte maturation followed by induced ovulation with an injection of 750 U of human chorionic gonadotropin (hCG), 4–5 days following the PMSG injection.

Eggs were de-jellied by incubation for 10–20 min at room temperature in 2% cysteine-HCl, pH 7.7 solution, and washed with extraction buffer containing 100 mM KCl, 0.1 mM $CaCl_2$, 1 mM $MgCl_2$, 50 mM sucrose, and 10 mM HEPES-KOH, pH 7.7. About 1 ml of eggs were transferred to a 1.5 ml microcentrifuge tube and the tube was filled with Nyosil M20 (Nye Lubricants Inc., New Bedford, Mass.). After spinning 2 min at 2,000 rpm at 4° C., the supernatant buffer and oil were removed completely. The tube was centrifuged for 15 min at 10,000 rpm at 4° C. The middle layer extract was collected by side-puncturing the tube with a 25 gauge needle. The above method is adapted from Murray and Kirschner (Murray, A. W. and Kirschner, M. W., (1989) Nature 339: 275–280). The extract was supplemented with cytochalasin B (50 mg/L) and aprotinin (76 TIU/L) then further spun for 5 min. Again, the middle layer was collected by side-puncturing and treated with RNase A (0.1 mg/L) to deplete endogenous mRNA by incubation at 10° C. for 15 min followed by 10 min incubation at the same temperature with RNase inhibitor (500 U/ml) and dithiothreitol (DTT, 1 mM) to inactivate ribonuclease activity. After supplementing with calf tRNA (100 mg/L) and glycerol (5%) or (preferably) sucrose (250 mM), the Xenopus egg extract was aliquoted and stored at –70° C. for later use.

Cell-Free Transcription/Translation, Translocation and Processing of Egg Extract Approximately 0.5–1 μg of various mRNAs were added to rabbit reticulocyte lysate, with RNase inhibitor and with amino acid mixture minus methionine in a final volume of 25 μl, according to manufacturer's instruction. If cDNA plasmid was used, then the appropriate RNA polymerase was included (e.g., SP6 RNA polymerase). The translation products were radiolabeled with the addition of [$^{35}$S] methionine (20 μCi/reaction) and translocation processing was induced with the addition of varying amounts of canine pancreatic microsomal membranes or Xenopus egg extract. The reactions were performed for 1.5 h at 30° C., and stopped by placing the mixture in ice.

Protease Protection Assay

*Saccharomyces cerevisiae* α-factor translation/ translocation (RRL/XEE) reaction mixture was divided into three 7 μl aliquots. The first aliquot was mixed with 40 μl Triton X-100 buffer (1% Triton X-100, 100 mM NaCl, 2.5 mM EDTA, 25 mM Tris-HCl, pH 7.4), and the second and the third were mixed with non-Triton X-100 buffer (100 mM NaCl, 2.5 mM EDTA, 25 mM Tris-HCl, pH 7.4). 1 μl of Trypsin (1 mg/ml, 0.2 U) was added to the first and second aliquots. These three tubes were incubated for 1 h on ice, then 5 μl PMSF (200 mM, freshly made) and 5 μl Aprotinin (7.8 TIU/ml) were added to each of the tubes and the incubation was continued for another 15 min. 50 μl of 4× sample buffer were then added to each of the tubes and after 5 min boiling and 2 min spinning, 10 μl samples were examined by SDS-PAGE (12%) and fluorography.

Photographic Luciferase Activity Assay

The luciferase protein was synthesized and radiolabeled with [$^{35}$S]methionine in vitro, as described above, in the presence or absence of 1.5 μl Xenopus egg extract. Aliquots of 5 μl of luciferase translation reaction mixture were mixed with 50 μl luciferase assay reagent (Promega, Madison, Wis.). These mixtures were immediately exposed to Polaroid 667 film for 8 min in the dark room to capture the light emitted from luminescence reagent which indicates the luciferase activity.

SDS-PAGE and Fluorography

All radiolabeled translation products were analyzed by SDS-PAGE using the discontinuous method of Laemmli (Laemmli (1970) Nature 227:680–685). Fluorography was performed with Enhance (Dupont NEN) followed by exposing to Fuji medical X-ray film overnight at –70° C.

Results

Co-Translational Processing Efficiency of Xenopus Egg Extract

To examine the co-translational processing efficiency of Xenopus egg extract, the *E. coli* β-lactamase and *S. cerevisiae* α-factor mRNA were translated in RRL with and without Xenopus egg extract. The β-lactamase is a secretory protein with a 2 kDa N-terminal signal sequence in its 31 kDa nascent polypeptide which is cleaved by signal peptidase to produce the 29 kDa mature enzyme. The yeast α-mating factor is also processed by signal peptide cleavage, but undergoes N-linked core glycosylation processing for the 18 kDa precursor to yield the 28 kDa processed form.

The signal sequence processing control protein, *E. coli* β-lactamase, and glycosylation control protein, *S. cerevisiae* α-factor, were synthesized in rabbit reticulocyte lysate with and without the addition of Xenopus egg extract. [$^{35}$S] methionine was used to label the translation product. Aliquots of the reaction mixtures were examined by 12% SDS-PAGE and fluorography.

As shown in FIG. 1, β-lactamase synthesized without Xenopus egg extract resulted in a predominant 31 kDa band which represents the β-lactamase precursor, but in the lane containing β-lactamase synthesized with Xenopus egg extract, a faster migrating 29 kDa band was observed, indicating that signal peptide cleavage of the precursor protein was induced by ER-equivalent components in Xenopus egg extract. The persistence of a weak band of 31 kDa in the sample lane representing β-lactamase synthesized with Xenopus egg extract is due to incomplete processing. Its intensity compared to the much stronger 29 kDa band reflects an apparent processing efficiency of greater than 95%.

FIG. 1 also indicates that RRL translation of the α-factor resulted in the identification of a single band of 18 kDa. The addition of Xenopus egg extract in the translation reaction produced a slower migrating band of 28 kDa. The processing efficiency is similar to that for β-lactamase; the addition of Xenopus egg extract resulted in near complete processing of precursor components. Thus, the data demonstrated that Xenopus egg extract is capable of efficient signal peptide cleavage and core glycosylation processing and that the combined use of RRL and Xenopus egg extract resulted in an efficient cell-free translation/translocation system.

Trypsin Protease Protection Assay

To further investigate the integrity of the ER equivalent microsomal membranes in Xenopus egg extract, a trypsin protease protection assay was performed on the α-factor synthesized with RRL/XEE. S. cerevisiae α-factor was translated and processed in reticulocyte lysate with Xenopus egg extract, as described above, and aliquots of the reaction mixture were incubated with trypsin (20 μg/ml) for 1 h on ice in the presence or absence of Triton X-100 (0.7% v/v). Following treatment, the [$^{35}$S]methionine-labeled translation products were examined by 12% SDS-PAGE and fluorography.

Figure 2:
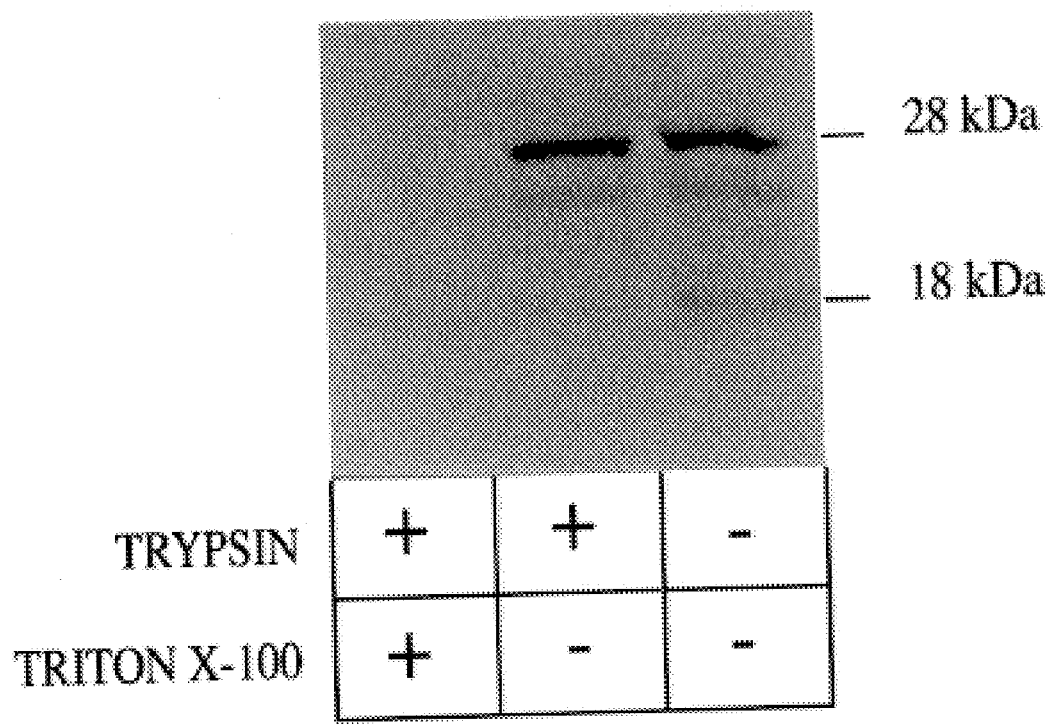
FIG. 2 is a gel from SDS-PAGE, representing protease protection of Xenopus egg extract processed α-factor.

As seen in FIG. 2, no radiolabeled 28 or 18 kDa bands of the α-factor were observed in the presence of Triton X-100. In contrast, a 28 kDa band of processed α-factor was observed in the trypsin-treated sample without Triton X-100. Since Triton X-100 disrupts the lipid bilayer structure, the persistence of the 28 kDa processed α-factor protein band in the sample without Triton X-100, but not with Triton X-100, indicates that the protection is afforded by the segregation of α-factor into intact microsomes in Xenopus egg extract. The digestion protection assay provides a reliable indication of the integrity of the endoplasmic reticulum equivalent membranes in Xenopus egg extract.

Figure 3:
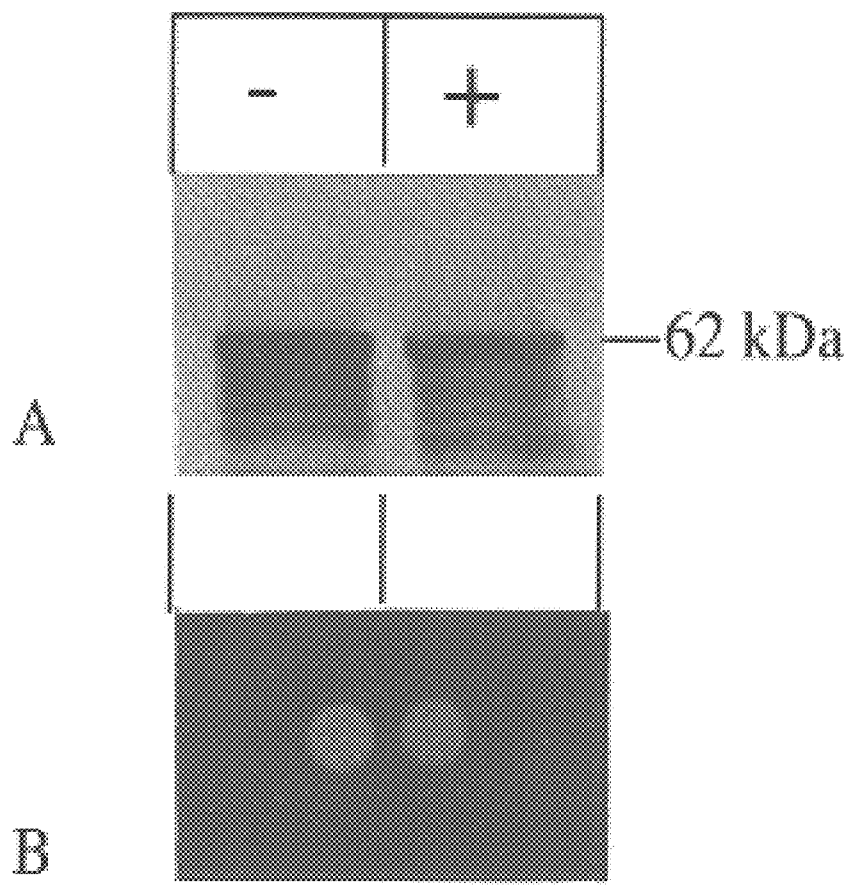
FIG. 3 is a gel from SDS-PAGE, providing a comparison of the luciferase translation and activity with and without Xenopus egg extract.

Effect of Xenopus Egg Extract on the Maturation of a Soluble Protein Translated by RRL It is known that a soluble protein can be translated in RRL and mature into its functional state. To study the effect of Xenopus egg extract in the maturation of a soluble protein translated by RRL, we chose luciferase as a model protein because it is easy to measure the luciferase's luminesence activity and the folding pathway of this protein in RRL is well documented (Frydman, J., et al. (1994) Nature 370:111; Frydman, J. and Hartl, F. U., (1996) Science 272:1497–1502). 1 μg of luciferase mRNA was added into 17 μl of RRL with or without 1.5 μl of Xenopus egg extract. The translation products were labeled by [$^{35}$S]methionine. The translation yield was judged by comparing the intensity of their bands in 12% SDS-PAGE. (FIG. 3, panel A). Their chemiluminescence activities were assessed by a photographic luciferase assay. A 5 μl aliquot of the reaction mixtures was assayed for chemiluminescence activity by photographic capture of light emitted from luminescence reagent in the presence of the reaction mixture (FIG. 3, panel B). As shown in FIG. 3, the intensities of luciferase presented by SDS-PAGE bands (panel A) and by luminesence-produced images (panel B) in both samples, with and without Xenopus egg extract, appeared to be the same. The data indicate that Xenopus egg extract has no effect on soluble protein luciferase's translation and maturation in RRL. This property allows the use of the RRL/XEE system to characterize any gene product, without prior knowledge of whether it is a soluble or membrane-bound protein.

XEE Processing Efficiency on High Molecular Weight Membrane-Bound Protein

To study Xenopus egg extract's processing efficiencies on high molecular weight membrane-bound protein and to assess the processing consistency between different preparations of Xenopus egg extract from different frogs, human insulin receptor was synthesized in RRL in different concentrations and batches of Xenopus egg extract. The [$^{35}$S] methionine labeled translation products were examined by 7% SDS-PAGE under reducing conditions.

The newly translated human insulin receptor nascent polypeptide results in a 160 kDa band. The processed proreceptor migrates at the 190 kDa position, in which the molecular weight shift is due to the attachment of sugar side chains to the receptor precursor by core glycosylation activity of Xenopus egg extract. As a control for the post-translational processing, commercially supplied microsomal membranes were used to perform a set of similar reactions (Goldstein, B. J. and Kahn, C. R. (1988) J. Biol. Chem. 263:12809–12.).

Figure 4:
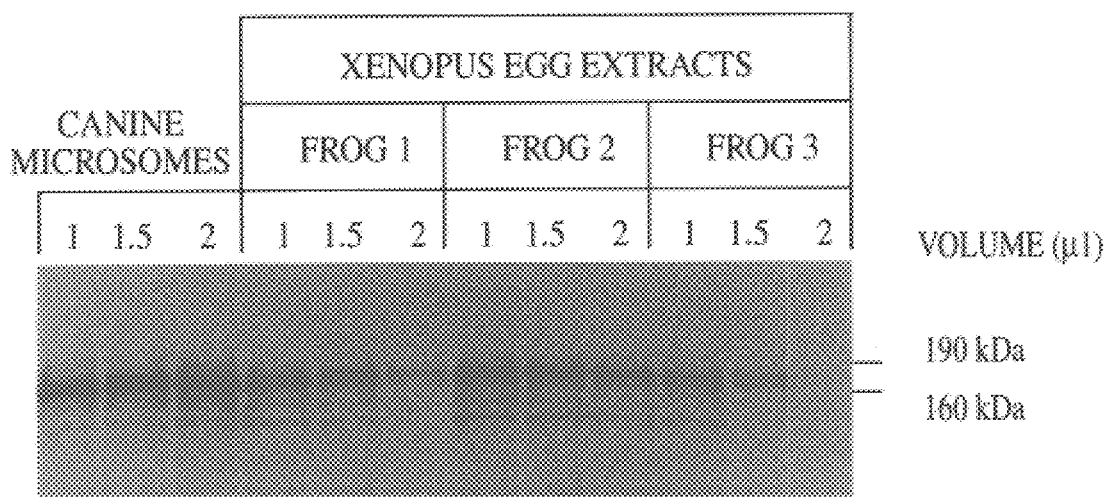
FIG. 4 is a gel from SDS-PAGE, representing post-translational processing of the human insulin proreceptor by Xenopus egg extract.

As shown in FIG. 4, as measured by the mobility patterns of 160 and 190 kDa bands on SDS-PAGE, there was near complete processing in the sample of 2 μl of Frog 2 Xenopus egg extract. In all the lanes of the three preparations of Xenopus egg extract processing samples, the processing efficiencies were greater than 50%. For different batches of Xenopus egg extract, the optimal concentrations for processing varied narrowly between 1 to 2 μl in a 25 μl translation reaction, despite the fact that different batches of Xenopus egg extract were from different frogs or from different cycles of hormone-induced ovulation. In contrast, the processing efficiency of canine microsomal membranes was less than 50%.

Example 2

Effect of DMSO on Canine Pancreatic Microsome and XEE Protein Translocation and Processing Dimethylsulfoxide (DMSO) is a dipolar, aprotic molecule used as a solvent to enhance certain organic reactions. This compound has additional qualities of aqueous interaction which allows for solubility of a number of organic products in an aqueous solution. DMSO has the unique property of penetrating and replacing the water content of cells without causing significant cellular damage. DMSO has been used extensively as a cryopreservative for freezing and storage of cells. In culture medium with approximately 8% concentration (vol/vol) of DMSO, many cells are stored frozen for prolonged periods of time and are viable when thawed later. Dimethylsulfoxide has also served as a vehicle to make available various organic compounds to cells, or for percutaneous adsorption in toxicity studies. For example, tritiated myristic and palmitic acids are dissolved in DMSO, and placed in media for cellular uptake and incorporation into proteins such as oncogenes and receptors i.e. src oncogene product and the insulin receptor. Despite its many uses, the adverse effect of DMSO on various cellular processing steps have not been thoroughly defined. Cellular changes such as condensation of chromatin and plasma membrane disruption have been ultrastructurally observed in cells frozen and thawed after pretreatment with DMSO. We have examined the direct effect of DMSO on RRL translation, and XEE and canine pancreatic microsome processing of the hINSR.

The addition of DMSO, approximately 8% of total reaction volume, in the translation reaction with canine pancreatic microsomes resulted in the complete absence of the 190 kDa band which primarily represents the N-linked glycosylated proreceptor. In addition, the radiolabeling intensity of the 160 kDa band was reduced. The absence of the 190 kDa band in the presence of DMSO was attributed to the direct effect of the bipolar solvent on N-linked glycosylation processing of the 160 kDa hINSR precursor component. The effect of DMSO on reducing translation efficiency appeared to be independent of its effect on inhibiting the processing of the hINSR. Thus, DMSO inhibited both translation and microsomal membrane processing in a coupled cell-free transcription and translation reaction utilizing rabbit reticulocyte lysate. Signal sequence processing of β-lactamase appeared to be well preserved in the presence of DMSO.

In XEE-added RRL reactions, the effect of DMSO in translation and processing was minimal. At concentrations of 8% DMSO per reaction mixture, processing of the 160 kDa band to 190 kDa band of the hINSR precursor proteins occurred with approximately 60% efficiency. Translation efficiency was reduced in the presence of 8% DMSO, but to a lesser extent than that observed in RRL reactions containing microsomal membranes. With DMSO concentrations of 6% or less, the translation and processing of the hINSR precursor components were similar to that observed for reactions without DMSO. These results indicate that XEE translocation and processing of proteins synthesized in RRL was minimally disturbed by the addition of DMSO. Thus, for cell-free translation studies that require the addition of solvents such as DMSO, XEE is superior to canine pancreatic microsomes for protein translocation and processing.

From the above, it should be evident that the present invention provides for an efficient and consistent cell-free protein synthesis, translocation and processing system. It should be understood that the present invention is not limited to the specific compositions or methods shown nor to the particular uses of the compositions described. In light of the foregoing disclosure, it will be apparent to those skilled in the art that substitutions, alterations, and modifications are possible in the practice of this invention without departing from the spirit or scope thereof.

We claim:

1. A method for in vitro synthesis, translocation and processing of a peptide comprising the steps of:

a. adding mRNA to a cell-free translation system to obtain a translation product, wherein said cell-free translation system is not derived from an amphibian egg; and b. adding an amphibian egg extract to said cell-free translation system containing said translation product, whereby said translation product is translocated and processed to a protein.

2. The method of claim 1 wherein said amphibian egg extract is from *Xenopus laevis*.

3. The method of claim 1 wherein said cell-free translation system is selected from the group consisting of a rabbit reticulocyte lysate and a wheat germ translation system.

* * * * *